US 6,724,200 B2

(12) United States Patent
Fukuda (10) Patent No.: US 6,724,200 B2
(45) Date of Patent: Apr. 20, 2004

(54) APPARATUS FOR MEASURING THE BIOELECTRICAL IMPEDANCE OF A LIVING BODY

(75) Inventor: Yoshinori Fukuda, Tokyo (JP)

(73) Assignee: Tanita Corporation, Tokyo (JP)

( * ) Notice: Subject to any disclaimer, the term of this patent is extended or adjusted under 35 U.S.C. 154(b) by 10 days.

(21) Appl. No.: 10/086,876

(22) Filed: Mar. 4, 2002

(65) Prior Publication Data

US 2002/0079910 A1 Jun. 27, 2002

Related U.S. Application Data (63) Continuation of application No. 09/642,006, filed on Aug. 21, 2000, now abandoned.

(30) Foreign Application Priority Data

Aug. 26, 1999 (JP) .............................. 11-239073

(51) Int. Cl.[7] .......................... G01R 27/08; A61B 5/05
(52) U.S. Cl. ...................... 324/692; 324/691; 324/715; 600/547
(58) Field of Search ................................ 324/692, 693, 324/715, 628, 713, 627; 600/506, 547; 606/32

(56) References Cited

U.S. PATENT DOCUMENTS

| 3,871,359 A | | 3/1975 | Pacela ......................... 600/547 |
| 5,503,157 A | * | 4/1996 | Sramek ........................ 600/506 |
| 5,818,243 A | * | 10/1998 | Wakamatsu .................. 324/649 |

FOREIGN PATENT DOCUMENTS

JP    3-228738    10/1991

OTHER PUBLICATIONS

Rigaud et al. "Bioelectrical Impedance Techniques in Medicine", US, CRC Press, vol. 24, NR. 4–06, pp. 257–336, 1996.*
"Bioelectrical Impedance Techniques in Medicine", Rigaud et al., Critical Reviews in Biomedical Engineering, US, CRC Press, vol. 24, NR. 4–06, pp. 257–336, 1996.
"Nutritional Assessment: Whole Body Impedance and Body Fluid Compartments", Settle et al., Nutrition and Cancer, vol. 2, No. 1, 1980, pp. 72–80.
"Multi–Frequency Static Imaging in Electrical Impedance Tomography Part 1: Instrumentation Requirements", Riu et al., Medical and Biological Engineering and Computing, vol. 33, No. 6, Nov. 1, 1995, pp. 784–792.
"Patient–instrument connection errors in bioelectrical impendance measurement", Feras Al–Hatib, Physiological Measurement, vol. 19, No. 2, May 1998, pp. 285–296.
European Search Report, Application No. EP 00 11 8117, Aug. 12, 2000.

* cited by examiner

*Primary Examiner*—Anjan K. Deb
(74) *Attorney, Agent, or Firm*—McDermott, Will & Emery (57) ABSTRACT

Disclosed is an improved bioelectrical impedance gauge which is so designed that the high-frequency current flowing between two selected points in a living body may be detected in the vicinity of either selected point, and that the voltage appearing between two points selected in the current passage in which the high-frequency current flows may be applied to a high-impedance buffer circuit proximate to the two points selected in the current passage.

15 Claims, 5 Drawing Sheets

APPARATUS FOR MEASURING THE BIOELECTRICAL IMPEDANCE OF A LIVING BODY

This application is a continuation of application Ser. No. 09/642,006 filed Aug. 21, 2000, now abandoned.

BACKGROUND OF THE INVENTION

1. Field of the Invention

The present invention relates to an apparatus for measuring the bioelectrical impedance of a living body in which the bioelectrical impedance can be determined by making a weak current of high-frequency flow from one to the other selected point in the living body, and by determining the weak current of high-frequency flowing through the current passage between the opposite selected points and the voltage appearing between another two selected points in the current passage in which the weak current flows.

2. Prior Art

Composition assessment of a selected portion of a living body in terms of its bioelectrical impedance is known from the magazine, "The American Journal of Clinical Nutrition", 41(4)810–817 1985, "Assessment of fat-free mass using bioelectrical impedance measurement of the human body". Also, an apparatus for analyzing the composition in a selected portion of a living body in terms of the bioelectrical impedance appearing in the selected portion is described in the magazine, "Journal of Applied Physiology VOL77 NO.1, Segmental bioelectrical analysis: theory and application of a new technique". Specifically, the bioelectrical impedance is determined by making electric current of high-frequency flow between the opposite terminal points of both hands and both feet and by measuring the voltage appearing between another two selected points in the current passage in which the weak current flows. A similar apparatus is disclosed in Japanese Patent Application Laid-Open No.10-510455.

Figure 5:
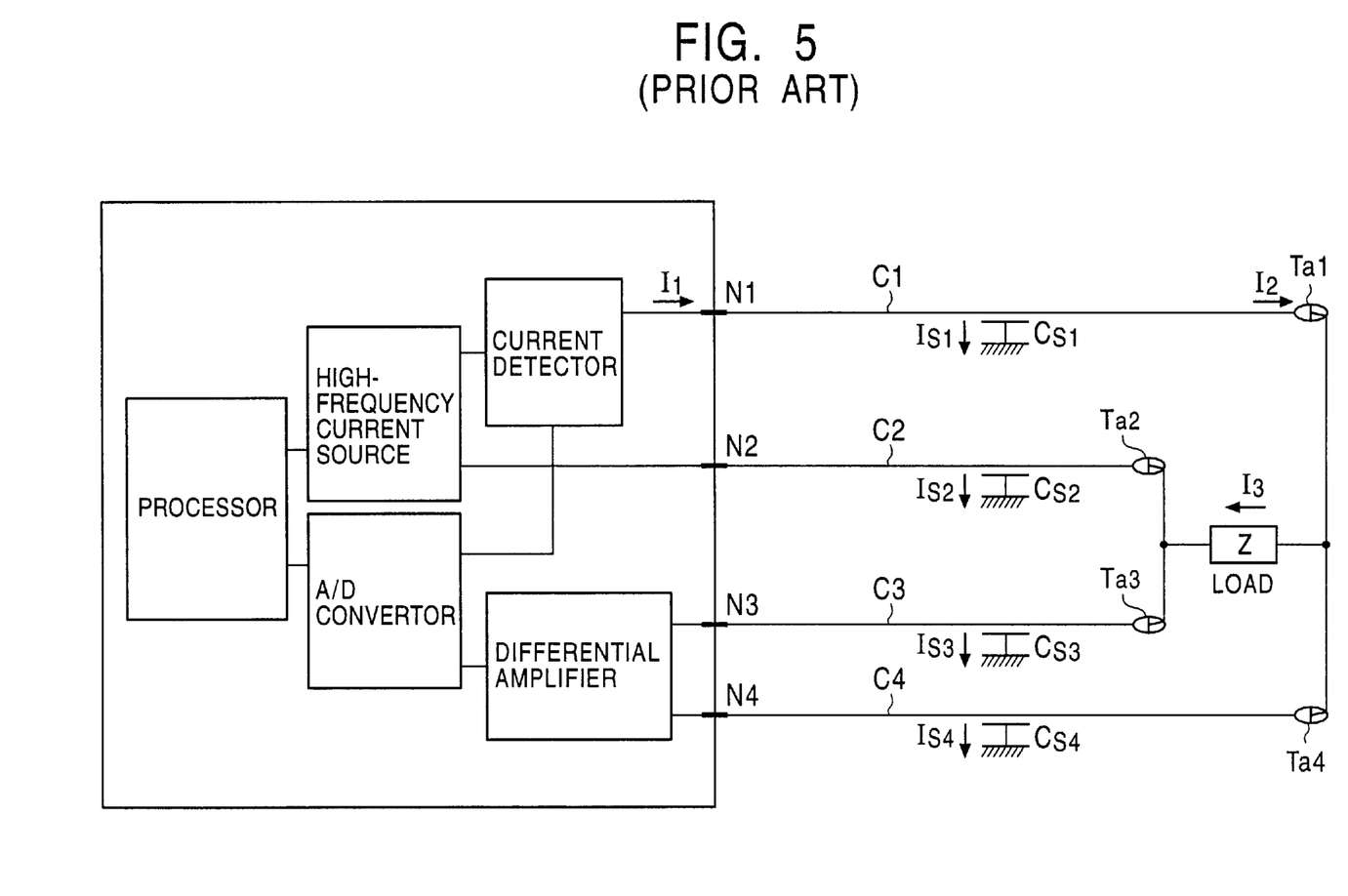
FIG. 5 is a block diagram showing the structure of a conventional biolectrical impedance gauge.

In such a conventional bioelectrical impedance gauge a weak current of high-frequency is made to flow in a living body; and the voltage appearing across a given length of current path in which the weak current flows is determined, as seen from FIG. 5.

Referring to FIG. 5, one terminal end of a load Z, which represents a portion selected in a living body, is connected both to the proximal end Ta1 of a high-frequency current supplying cable C1 and to the proximal end Ta4 of a voltage-measuring cable C4 whereas the other terminal end of the load Z is connected both to the proximal end Ta2 of another high-frequency current supplying cable C2 and to the proximal end Ta3 of another voltage-measuring cable C3. Each cable C1, C2, C3 or C4 has its stray capacitance $Cs_1$, $Cs_2$, $Cs_3$ or $Cs_4$ appearing between the cable and the ground. These stray capacitances will have an adverse effect on the measurement.

Different currents appearing on the current supplying side of the impedance gauge of FIG. 5 are given as follows:

$$I1=I2+Is1$$

where I1 stands for the electric current flowing from the impedance gauge to the high-frequency current supplying cable C1 (the current being measured by a current detector); I2 stands for the electric current passing through the proximal end Ta1 of the high-frequency current supplying cable C1; and Is1 stands for the electric current flowing through the stray capacitance $Cs_1$ of the high-frequency current supplying cable C1.

The electric current Is4 flows through the stray capacitance $Cs_4$, which appears between the voltage-measuring cable C4 and the ground. The electric current I3 flows in the load. Assuming that the input impedance as seen inward from the voltage measuring terminals N3 and N4 of the impedance gauge is infinitively large, and that the impedance of each cable is zero, the electric current I2 is given by:

$$I2=I3+Is4.$$

Thus, the electric current I3 flowing in the load is given by:

$$I3=I1-Is1-Is4$$

The current I1 flowing from the impedance gauge into the high-frequency current supplying cable C1 (measured by the current detector) cannot be equal to the current I3 passing through the impedance Z, thus causing an error in measurement. As a matter of fact, the impedance measured by the impedance gauge is smaller than the impedance of the load Z.

Such an error can be corrected to some extent, but no satisfactory correction can be made; as the cables change in position, their stray capacitances vary. Thus, the measurement will be adversely affected, and the adverse effect is apt to increase with the increase both of the frequency of the electric current and of the cable length.

It takes a significant time for the current signal I1 to flow from one terminal N1 to the other terminal N2 through the out-going high-frequency current supplying cable C1, the load Z and the in-coming high-frequency current supplying cable C2, allowing this delay time to appear as phase lag, which is proportional to the frequency of the electric current flowing in the load Z, thus contributing to the error in the measurement.

SUMMARY OF THE INVENTION

In view of the above one object of the present invention is to provide an improved apparatus for measuring the bioelectrical impedance of a living body, which apparatus is guaranteed to be free of the adverse effect caused by the stray capacitances and lengths of associated cables, thus permitting the exact measurement of bioelectrical impedance over an expanded range from low to high frequencies.

To attain this object an apparatus for measuring the bioelectrical impedance of a living body in which the impedance of the living body can be determined by making a weak electric current of high-frequency flow between two selected points on the living body and by determining the voltage between said two selected points or between another two points selected in the current passage in which the weak electric current flows_ is improved according to the present invention in that it comprises: a measuring apparatus including a high-frequency current source, a high-frequency current determining section and a voltage determining section; at least one high-frequency current supplying probe connected to said high-frequency current source via a shielded-conductor cable; a pair of high-frequency current supplying electrodes to be applied to said two selected points; two voltage measuring probes connected to said voltage determining section via shielded-conductor cables; and a pair of voltage measuring electrodes to be applied to said two selected points or said another two points, said high-frequency current supplying probe having a high-frequency current detector connected to and positioned in the vicinity of one of said pair of high-frequency current supplying electrodes.

An apparatus for measuring the bioelectrical impedance of a living body in which the impedance of the living body can be determined by making a weak electric current of high-frequency flow between two selected points on the living body and by determining the voltage between said two selected points or between another two points selected in the current passage in which the weak electric current flows, is improved according to the present invention in that it comprises: a measuring apparatus including a high-frequency current source, a high-frequency current determining section and a voltage determining section; at least one high-frequency current supplying probe connected to said high-frequency current source via a shielded-conductor cable; a pair of high-frequency current supplying electrodes to be applied to said two selected points; two voltage measuring probes connected to said voltage determining section via shielded-conductor cables; and a pair of voltage measuring electrodes to be applied to said two selected points or said another two points, each of said voltage measuring probes having a high input-impedance amplifier connected to and positioned in the vicinity of one or the other voltage measuring electrode.

Two high-frequency current supplying probes may be connected to said high-frequency current source via shielded-conductor cables.

One high-frequency current supplying probe may be connected to said high-frequency current source via a shielded cable, said high-frequency current supplying probe having a high-frequency current detector connected to and positioned in the vicinity of one of the high-frequency current supplying electrodes, and the other high-frequency current supplying electrode being directly connected to said high-frequency current source.

Said high-frequency current detector may comprise a protection circuit connected to one or the other high-frequency current supplying electrode, a reference resistor for detecting the high-frequency current, said reference resistor being connected to said protection circuit at one end, and to said high-frequency current source at the other end via the shielded-conductor cable, and a differential amplifier the input terminals of which are connected across said reference resistor, and the output terminal of which differential amplifier is connected to said high-frequency current determining section via the shielded-conductor cable and an associated impedance matching resistor.

Said high input-impedance amplifier may comprise a protection circuit connected to one or the other voltage measuring electrode, a high-input impedance buffer circuit connected at its input terminal to said protection circuit and at its output terminal to said voltage determining section via the shielded-conductor cable and an associated impedance matching resistor.

All shielded cables may be of same length.

With the arrangements described above the electric current flowing just ahead of one or the other selected point of the living body can be measured, thereby eliminating any errors which otherwise, would be caused by the stray capacitances of the cables. Positioning the high-input impedance buffer circuit close to the voltage determining electrode and making an electric connection thereto effectively minimizes the passage to the infinitely high-impedance input for voltage-representative signals to follow, accordingly reducing the adverse effect caused on the way by the surrounding disturbance or noise signals. The flowing of the impedance-representative currents into the impedance gauge via the impedance-matched, shielded-conductor cables effectively minimizes the adverse effect caused by the surrounding disturbance or noise signals. Finally, use of cables of equal length in which the impedance-representative currents flow makes their transmission time equal, so that the signal delays may be cancelled to eliminate such a phase lag as would be caused if the cables of different lengths were used.

Other objects and advantages of the present invention will be understood from the following description of bioelectrical impedance gauges according to preferred embodiments of the present invention, which are shown in accompanying drawings:

DESCRIPTION OF PREFERRED EMBODIMENTS

Figure 1:
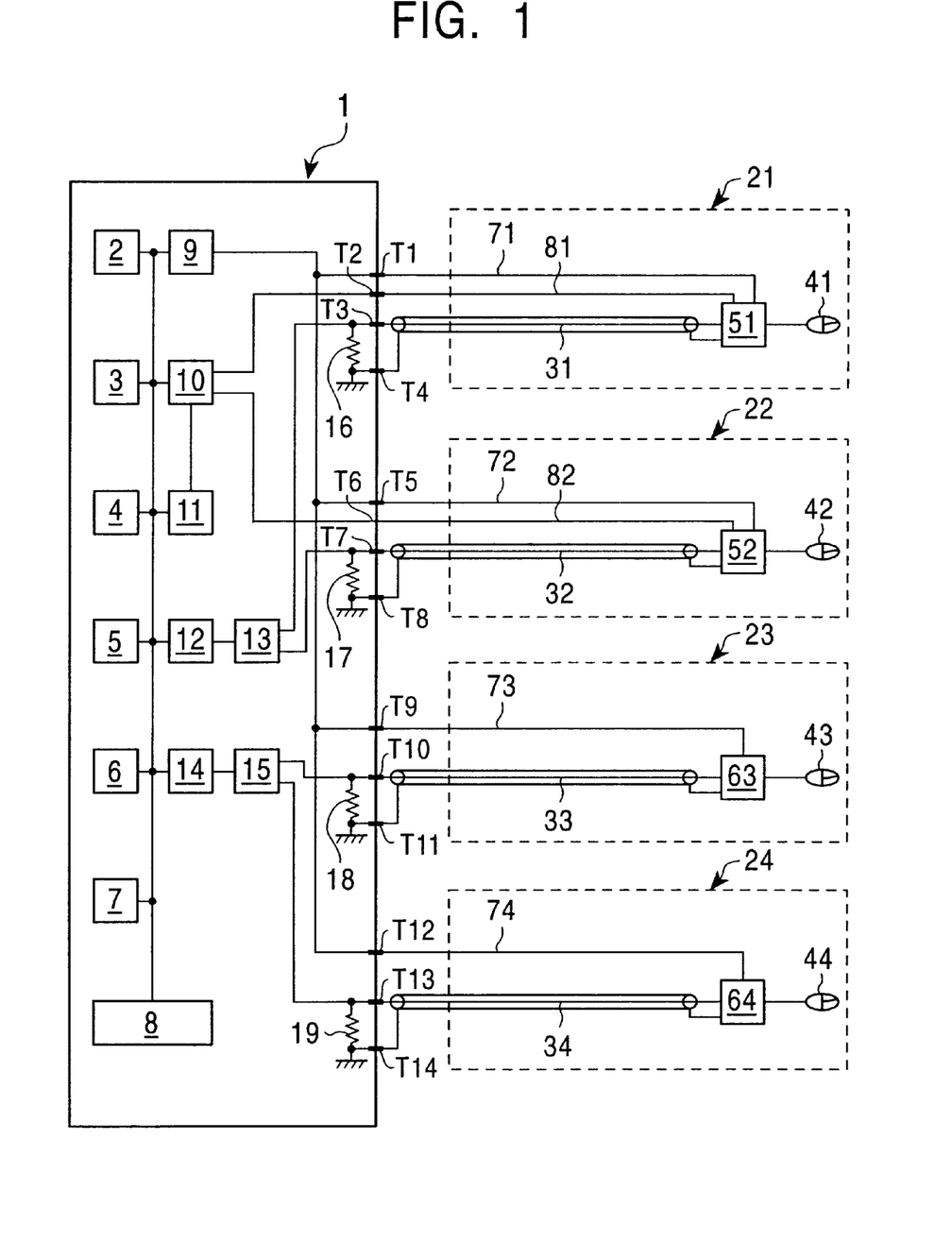
FIG. 1 is a block diagram showing the structure of a bioelectrical impedance gauge according to a first embodiment.

Referring to FIG. 1, a bioelectrical impedance gauge according to the first embodiment (the so measured bioelectrical impedance being used in analyzing and assessing some components of the living body) comprises mainly a gauge center 1, a pair of high-frequency current supplying probes 21, 22 for supplying two points selected in a living body with a high-frequency current, and a pair of voltage measuring probes 23, 24 for measuring the voltage appearing between another two points selected in the current passage in which the high-frequency current.

The gauge center 1 includes a control-and-arithmetic operation processing unit 8 for controlling the whole operation of the bioelectrical impedance gauge and for processing the arithmetic operation on measured data, a ROM 2 connected to the control-and-processor 8 for storing the controlling and processing software programs, a RAM 3 for storing the data provided by measurement and the software program for arithmetic operation, an auxiliary memory 4 for storing of the record of the data provided by measurement, an input/output interface 5 for inputting control signals required for controlling the bioelectrical impedance gauge and for outputting the data provided by measurement, a keyboard 6 for inputting measurement start instructions, different parameters and such like, a display device 7 for indicating the instantaneous operation of the bioelectrical impedance gauge and the results of measurement, a power supply 9 for supplying different parts of the bioelectrical impedance gauge with electric power, a high-frequency signal generator 11 for generating high-frequency signals under the control of the control-and-processor 8, a high-frequency current source 10 responsive to the high-frequency signals from the high-frequency signal generator 11 for providing a high-frequency electric current of a given fixed effective value, a differential amplifier circuit 13 for amplifying the high-frequency electric current flowing in a living body, another differential amplifier circuit 15 for amplifying the electric potential difference between two selected points in the living body, analog-to-digital converters 12 and 14 for converting analog signals representing the electric current and electric potential difference provided by measurement to corresponding digital data, and impedance matching resistors 16, 17, 18 and 19. As shown in FIG. 1, the high-frequency current supplying probes 21, 22 are connected to the high-frequency current source 10 and the differential amplifier 13, and to the power supply 9 whereas the voltage measuring probes 23, 24 are connected to the differential amplifier 15 and to the power supply 9.

Each high-frequency current supplying probe 21 or 22 comprises an electrode 41 or 42 to be applied to one or the other selected point in the living body for supplying it with a high-frequency current, a high-frequency current supplying cable 81 or 82, a current detector 51 or 52 for detecting the high-frequency electric current flowing in the living body, a power cable 71 or 72 for supplying the probe with electric power, and a shielded-conductor cable 31 or 32 connecting the detector 51 or 52 to the differential amplifier 13 in the gauge center 1. The current detector 51 or 52 is connected to the electrode 41 or 42 via such a possible shortest length of cable that the electric current to be detected may be guaranteed to be free of any exterior adverse effects, thus permitting the current detector to measure exactly the electric current flowing from one to the other selected point in the living body.

Each voltage measuring probe 23 or 24 comprises an electrode 43 or 44 to be applied to one or the other point selected in the current passage in which the high-frequency current flows for detecting the voltage between the two selected points in the current passage, a high-input impedance amplifier 63 or 64, a power cable 73 or 74 for supplying the probe with electric power, and a shielded-conductor cable 33 or 34 connecting the amplifier 63 or 64 to the differential amplifier 15 in the gauge center 1. The amplifier 63 or 64 is connected to the electrode 43 or 44 via such a possible shortest length of cable that the electric current to be amplified may be guaranteed to be free of any exterior adverse effects, thus permitting the amplifier to have the exact voltage appearing between the two selected points in the living body.

All shielded-conductor cables 31, 32, 33 and 34 are of same length.

Figure 2:
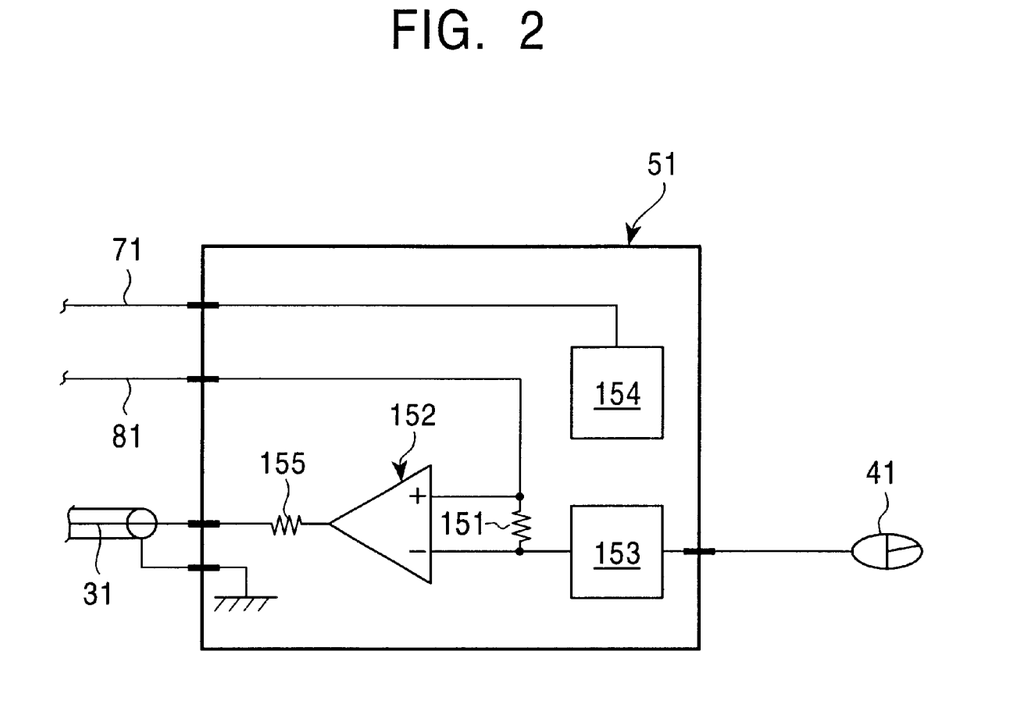
FIG. 2 shows some details of the current detector of the high-frequency current supplying probe.

Referring to FIG. 2, the high-frequency current detector 51 or 52 of each high-frequency current supplying probe 21 or 22 comprises a protection circuit 153 connected to one or the other high-frequency current supplying electrode 41 or 42, a reference resistor 151 for detecting the high-frequency current, a differential amplifier 152, an impedance matching resistor 155 and a power supply circuit 154 for supplying different parts with electric power. The protection circuit 153 includes for instance, diode circuits to prevent the flowing of such an increased current as would give electric shock to the living body. The resistor 155 attains the impedance-matching between the differential amplifier and the shielded-conductor cable 31. The reference resistor 151 is connected to the protection circuit 153 at one end, and to the high-frequency current source 10 at the other end via the shielded-conductor cable 31 or 32. The differential amplifier 152 is connected across the reference resistor 151 on its input side, and to the differential amplifier 13 via the impedance matching resistor 155 and the shielded-conductor cable 31 or 32.

Figure 3:
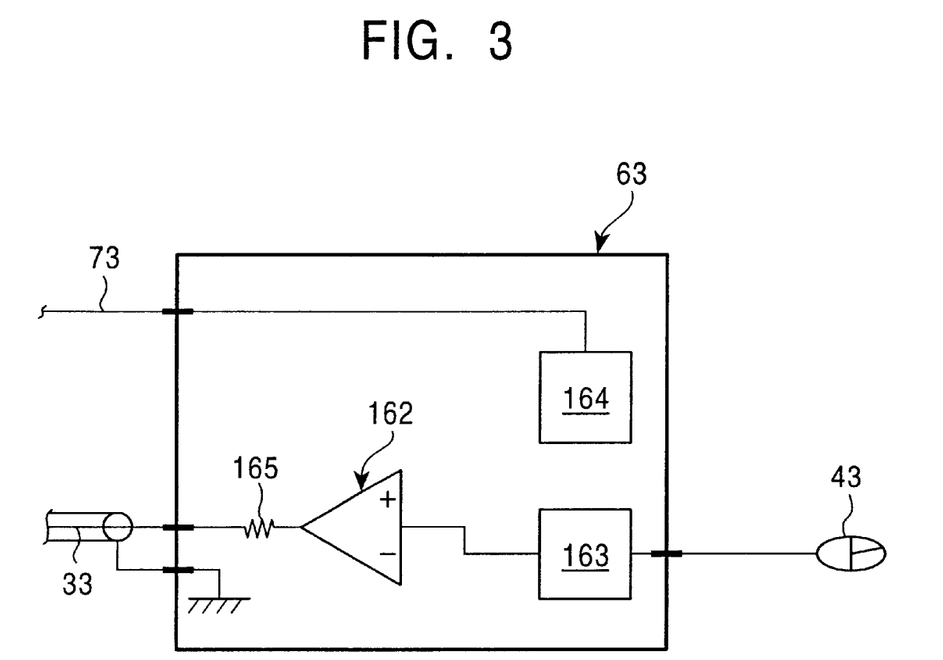
FIG. 3 shows some details of the high-input impedance amplifier of the voltage measuring probe.

Referring to FIG. 3, the high-impedance amplifier 63 or 64 of each voltage measuring probe 23 or 24 comprises a protection circuit 163 connected to one or the other voltage measuring electrode 43 or 44, a high-impedance buffer circuit 162, an impedance matching resistor 165 and a power supply circuit 164 connected to the power supply 9 of the gauge center 1 for supplying different parts with electric power. The protection circuit 163 includes for example, diodes to effectively prevent application of destructive electrostatic potential to the high-impedance buffer circuit 162. The voltage-representative signal from the voltage measuring electrode 43 is allowed to pass from the protection circuit 163 to the differential amplifier 15 of the gauge center 1 via the high-impedance buffer circuit 162, the cable-impedance matching resistor 165 and the shielded-conductor cable 33.

In operation the high-frequency current supplying electrodes 41 and 42 of the high-frequency current supplying probes 21 and 22 are applied to two points selected in a living body to make a fixed high-frequency current flow between the opposite electrodes 41 and 42 under the control of the control-and-processor 8.

The high-frequency current is detected ahead of one or the other electrode 41 or 42 just prior to entrance to the living body in terms of the voltage appearing across the reference resistor 151, and then, the current-representative signal is allowed to pass to the differential amplifier 13 in the gauge center 1 via the shielded-conductor cable 31 or 32. The current-representative signal thus appearing at the output terminals of the differential amplifier 13 is converted to digital form to be stored in the RAM 3 of the gauge center 1. The so stored information represents the exact value of the high-frequency current flowing in the passage between the two selected points in the living body because the detected high-frequency current is guaranteed to be free of any adverse effect caused by the cable-to-ground stray capacitances and by any surrounding disturbance or spurious signals.

Likewise, the voltage measuring electrodes 43 and 44 of the voltage measuring probes 23 and 24 are applied to another two points selected in the current passage in which the weak current flows to detect the voltage appearing between the opposite electrodes 43 and 44.

The voltage is detected by the high-impedance amplifier 63 or 64, which is connected to and placed close to one or the other electrode 43 or 44 in the vicinity of either selected point in the living body, and then, the voltage-representative signal is allowed to pass to the differential amplifier 15 in the gauge center 1 via the shielded-conductor cable 33 or 34. The voltage-representative signal thus appearing at the output terminals of the differential amplifier 15 is converted to digital form to be stored in the RAM 3 of the gauge center 1. The so stored information represents the exact value of the voltage appearing across the given length of current passage in the living body because the detected voltage is guaranteed to be free of any adverse effect caused by any surrounding disturbance or spurious signals; the high-input impedance buffer circuit 162 has a possible shortest passage permitting the voltage-representative signal to follow on its input side, and the voltage-representative signal is permitted to travel on the shielded-conductor cable whose impedance is exactly matched to the impedance as seen from the output side of the buffer circuit 162.

The arithmetic operation is effected on the current- and voltage-representative data stored in the RAM 3 according to the software program stored in the ROM 2 to provide the bioelectrical impedance appearing between the two selected points in the living body.

Figure 4:
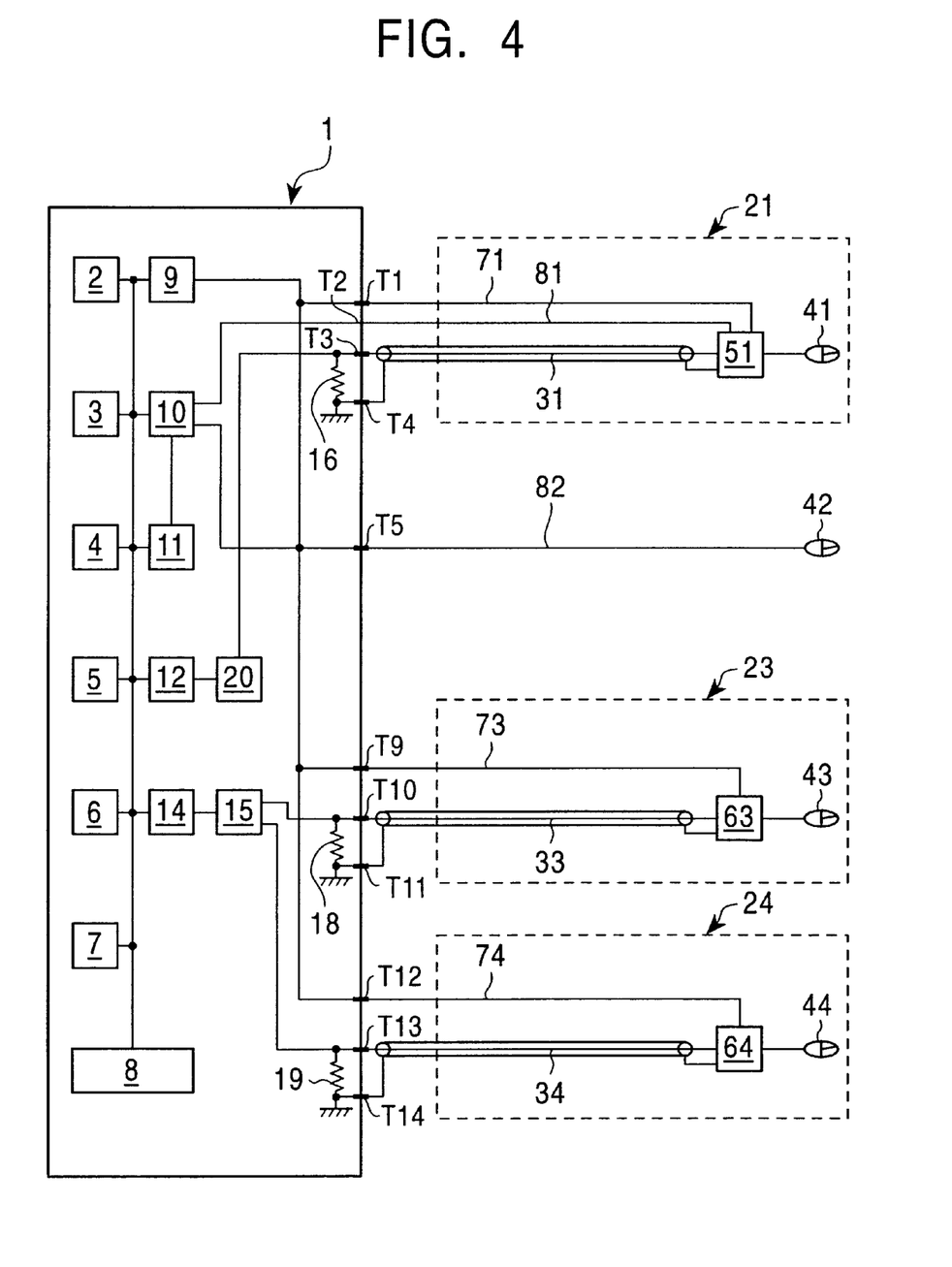
FIG. 4 is a block diagram showing the structure of a bioelectrical impedance gauge according to a second embodiment.

FIG. 1 shows a bioelectrical impedance gauge as using two high-frequency current supplying probes. As shown in FIG. 4, a bioelectrical impedance gauge may use a single high-frequency current supplying probe, the remaining electrode being connected directly to the high-frequency current measuring section of the gauge center via an associated high-frequency current supplying cable.

FIGS. 1 and 4 show the basic structure of the bioelectrical impedance gauge according to the present invention. The bioelectrical impedance gauge structure may be so modified that four high-frequency current supplying probes and four voltage measuring probes may be applied to both hands and both feet, and that an electrode-switching device may be used to permit electrodes to be selectively combined as desired.

As may be understood from the above, the high-frequency current is determined ahead of one or the other selected point at which the current is made to flow in the living body, thereby permitting determination of the exact value of the high-frequency current flowing in the living body, and the high-impedance buffer circuit positioned proximate to one or the other selected point permits significant reduction of the passage for the voltage-representative signal to follow, thereby minimizing the adverse effect caused by the surrounding disturbance. Use of cables of same length permits cancellation of delays in signal transmission, thus contributing minimization of errors, if any.

What is claimed is:

1. An apparatus for measuring the bioelectrical impedance of a living body in which the impedance of the living body can be determined by flowing a weak electric current of high-frequency between two selected points on the living body and determining the voltage appearing between another two points selected in the current passage in which the weak current flows, the apparatus comprising:
   a measuring apparatus (1) including a high-frequency current source (10), a high-frequency current determining section (13, 20) and a voltage determining section (15);
   at least one high-frequency current supplying probe (21, 22) connected to said high-frequency current source (10) via a high frequency current supplying cable (81, 82) and to said high-frequency current determining section (13, 20) via a shielded-conductor cable (31, 32);
   a pair of high-frequency current supplying electrodes (41, 42) to be applied to said two selected points; and
   a pair of voltage measuring electrodes (43, 44) to be applied to said another two points, said electrodes (43, 44) connected to said voltage determining section (15);
   wherein said at least one high-frequency current supplying probe (21, 22) has one of said pair of high-frequency current supplying electrodes (41, 42) and a high-frequency current detector (51, 52) connected to and positioned in the vicinity of said one of said pair of high-frequency current supplying electrodes (41, 42).

2. An apparatus for measuring the bioelectrical impedance of a living body according to claim 1 wherein two high-frequency current supplying probes (21, 22) are respectively connected to said high-frequency current source (10) via said high-frequency current supplying cables (81, 82) and to said high-frequency current determining section (13 or 20) via said shielded-conductor cables (31, 32).

3. An apparatus for measuring the bioelectrical impedance of a living body according to claim 1 wherein said high-frequency current supplying probe (21) has one of said pair of high-frequency current supplying electrodes (41) and a high-frequency current detector (51) connected to and positioned in the vicinity of said one of said pair of high-frequency current supplying electrodes (41), and the other of said pair of high-frequency current supplying electrodes (42) is directly connected to said high-frequency current source (10).

4. An apparatus for measuring the bioelectrical impedance of a living body according to claim 1 further comprising:
   at least one voltage measuring probe (23, 24) having one of said pair of measuring electrodes (43, 44) and a high input-impedance amplifier (63, 64) connected to and positioned in the vicinity of said one of said pair of measuring electrodes (43, 44);
   wherein said at least one voltage measuring probe (23, 24) is connected to said voltage determining section (15) via a shielded-conductor cable (33, 34).

5. An apparatus for measuring the bioelectrical impedance of a living body according to claims 1, 2, 3, or 4 wherein said high-frequency current detector (51) includes a protection circuit (153) connected to one or the other high-frequency current supplying electrode (41), a reference resistor (151) for detecting the high-frequency current, said reference resistor (151) being connected to said protection circuit (153) at one end, and to said high-frequency current source (10) at the other end via said high-frequency current supplying cable (81), and a differential amplifier (152) the input terminals of which are connected across said reference resistor (151), and the output terminal of which differential amplifier (152) is connected to said high-frequency current determining section (13, 20) via said shielded-conductor cable (31) and an associated impedance matching resistor (155).

6. An apparatus for measuring the bioelectrical impedance of a living body in which the impedance of the living body can be determined by flowing a weak electric current of high-frequency between two selected points on the living body and determining the voltage appearing between another two points selected in the current passage in which the weak electric current flows, the apparatus comprising:
   a measuring apparatus (1) including a high-frequency current source (10), a high-frequency current determining section (13, 20) and a voltage determining section (15);
   a pair of high-frequency current supplying electrodes (41, 42) to be applied to said two selected points and said electrodes (41, 42) connected to said high-frequency current source (10);
   at least one voltage measuring probe (23, 24) connected to said voltage determining section (15) via a shielded-conductor cables (33, 34); and
   a pair of voltage measuring electrodes (43, 44) to be applied to said another two points;
   wherein said at least one voltage measuring probe (23, 24) has one of said pair of voltage measuring electrodes (43, 44) and a high input-impedance amplifier (63, 64) connected to and positioned in the vicinity of said one of said pair of voltage measuring electrodes (43, 44).

7. An apparatus for measuring the bioelectrical impedance of a living body according to claim 6 further comprising:
   at least one high-frequency current supplying probe (21, 22) having one of said pair of high-frequency current supplying electrodes (41, 42) and a high-frequency current detector (51, 52) connected to and positioned in the vicinity of said one of said pair of high-frequency current supplying electrodes (41, 42);
   wherein said at least one high frequency current supplying probe (21, 22) is connected to said high-frequency current source (10) via a high-frequency current supplying cable (81 or 82) and to said high-frequency current determining section (13, 20) via a shielded-conductor cable (31, 32).

8. An apparatus for measuring the bioelectrical impedance of a living body according to claim 7 wherein said high-frequency current detector (51) includes a protection circuit (153) connected to one or the other high-frequency current supplying electrode (41), a reference resistor (151) for detecting the high-frequency current, said reference resistor (151) being connected to said protection circuit (153) at one end, and to said high-frequency current source (10) at the other end via said high-frequency current supplying cable (81), and a differential amplifier (152) the input terminals of which are connected across said reference resistor (151), and the output terminal of which differential amplifier (152) is connected to said high-frequency current determining section (13, 20) via said the shielded-conductor cable (31) and an associated impedance matching resistor (155).

9. An apparatus for measuring the bioelectrical impedance of a living body according to claim 6, 7, or 8 wherein said high input-impedance amplifier (63) comprises a protection circuit (163) connected to one or the other voltage measuring electrode (43), a high-input impedance buffer circuit (162) connected at its input terminal to said protection circuit (163) and at its output terminal to said voltage determining section (15) via said shielded-conductor cable (33) and an associated impedance matching resistor (165).

10. An apparatus for measuring the bioelectrical impedance of a living body according to any of claims 1, 2, 3, 4, 6, 7, or 8, wherein all shielded-conductor cables (31, 32, 33, 34) are of same length.

11. An apparatus for measuring the bioelectrical impedance of a living body in which the impedance of the living body can be determined by flowing a weak electric current of high-frequency between two selected points on the living body and determining the voltage appearing between another two points selected in the current passage in which the weak electric current flows, the apparatus comprising:

a measuring apparatus (1) including a high-frequency current source (10), a high-frequency current determining section (13, 20) and a voltage determining section (15);

at least one high-frequency current supplying probe (21, 22) connected to said high-frequency current source (10) via a high frequency current supplying cable (81, 82) and to said high-frequency current determining section (13, 20) via a shielded-conductor cable (31, 32);

a pair of high-frequency current supplying electrodes (41, 42) to be applied to said two selected points; and at least one voltage measuring probe (23, 24) connected to said voltage determining section (15) via a shielded-conductor cable (33, 34); and a pair of voltage measuring electrodes (43, 44) to be applied to said another two points;

wherein said at least one high-frequency current supplying probe (21, 22) has one of said pair of high-frequency current supplying electrodes (41, 42) and a high-frequency current detector (51, 52) connected to and positioned in the vicinity of said one of said pair of high-frequency current supplying electrodes (41, 42), and wherein said at least one voltage measuring probe (23, 24) has one of said pair of voltage measuring electrodes (43, 44) and a high input-impedance amplifier (63, 64) connected to and positioned in the vicinity of said one of said pair of voltage measuring electrodes (43, 44).

12. An apparatus for measuring the bioelectrical impedance of a living body according to claim 11 wherein said high-frequency current detector (51) includes a protection circuit (153) connected to one or the other high-frequency current supplying electrode (41), a reference resistor (151) for detecting the high-frequency current, said reference resistor (151) being connected to said protection circuit (153) at one end, and to said high-frequency current source (10) at the other end via said high-frequency current supplying cable (81), and a differential amplifier (152) the input terminals of which are connected across said reference resistor (151), and the output terminal of which differential amplifier (152) is connected to said high-frequency current determining section (13, 20) via said shielded-conductor cable (31) and an associated impedance matching resistor (155).

13. An apparatus for measuring the bioelectrical impedance of a living body according to claim 11 wherein said high input-impedance amplifier (63) comprises a protection circuit (163) connected to one or the other voltage measuring electrode (43), a high-input terminal to said protection circuit (163) and at its output terminal to said voltage determining section (15) via said shielded-conductor cable (33) and an associated impedance matching resistor (165).

14. An apparatus for measuring the bioelectrical impedance of a living body according to claim 11, wherein said high-frequency current detector (51) includes a protection circuit (153) connected to one or the other high-frequency current supplying electrode (41), a reference resistor (151) for detecting the high-frequency current, said reference resistor (151) being connected to said protection circuit (153) at one end, and to said high-frequency current source (10) at the other end via said high-frequency current supplying cable (81), and a differential amplifier (152) the input terminals of which are connected across said reference resistor (151), and the output terminal of which differential amplifier (152) is connected to said high-frequency current determining section (13, 20) via said shielded-conductor cable (31) and an associated impedance matching resistor (155), and wherein said high input-impedance amplifier (63) comprises a protection circuit (163) connected to one or the other voltage measuring electrode (43), a high-input impedance buffer circuit (162) connected at its input terminal to said protection circuit (163) and at its output terminal to said voltage determining section (15) via said shielded-conductor cable (33) and an associated impedance matching resistor (165).

15. An apparatus for measuring the bioelectrical impedance of a living body according to any one of claims 11, 12, 13, or 14 wherein all shielded-conductor cables (31, 32, 33, 34) are of the same length.

* * * * *